United States Patent
Aksela et al.

(10) Patent No.: US 11,225,456 B2
(45) Date of Patent: Jan. 18, 2022

(54) PROCESS FOR THE PREPARATION OF A MIXTURE OF CHELATING AGENTS, MIXTURE OF CHELATING AGENTS AND METHODS OF USING THEM

(71) Applicant: Kemira Oyj, Helsinki (FI)

(72) Inventors: Reijo Aksela, Espoo (FI); Jonas Konn, Espoo (FI); Anna-Maija Perander, Espoo (FI); Anna Haarala, Espoo (FI); Riitta Ilmoniemi, Kirkkonummi (FI); Hanna Hoffren, Helsinki (FI)

(73) Assignee: Kemira Oyj, Helsinki (FI)

(*) Notice: Subject to any disclaimer, the term of this patent is extended or adjusted under 35 U.S.C. 154(b) by 116 days.

(21) Appl. No.: 16/627,055

(22) PCT Filed: Jun. 27, 2018

(86) PCT No.: PCT/FI2018/050505
§ 371 (c)(1),
(2) Date: Dec. 27, 2019

(87) PCT Pub. No.: WO2019/002685
PCT Pub. Date: Jan. 3, 2019

(65) Prior Publication Data
US 2020/0181063 A1    Jun. 11, 2020

(30) Foreign Application Priority Data
Jun. 30, 2017 (FI) .................................. 20175632

(51) Int. Cl.
C07C 227/16 (2006.01)
C07C 229/12 (2006.01)
D21C 9/10 (2006.01)

(52) U.S. Cl.
CPC .......... *C07C 227/16* (2013.01); *C07C 229/12* (2013.01); *D21C 9/1042* (2013.01)

(58) Field of Classification Search
None
See application file for complete search history.

(56) References Cited

U.S. PATENT DOCUMENTS

| | | | |
|---|---|---|---|
| 6,590,120 B1 * | 7/2003 | Aksela | C01B 15/037 560/171 |
| 2010/0297460 A1 | 11/2010 | Kukkonen et al. | |
| 2014/0296113 A1 | 10/2014 | Reyes et al. | |

FOREIGN PATENT DOCUMENTS

| | | |
|---|---|---|
| EP | 1070045 A1 | 1/2001 |
| WO | 9745396 A1 | 12/1997 |
| WO | 9946234 A1 | 9/1999 |
| WO | 2011151517 A2 | 12/2011 |

OTHER PUBLICATIONS

Lutz, Matthias et al., Facile Synthesis of Novel Acyclic Polycarboxylic Acids, Zeitschrift fur Naturforschung B, Jan. 1, 2005, pp. 408-412.

* cited by examiner

*Primary Examiner* — Amy C Bonaparte
(74) *Attorney, Agent, or Firm* — Meunier Carlin & Curfman LLC

(57) ABSTRACT

The present invention relates to a process for in situ the preparation of mixtures of chelating agents by catalyzed reactions of diethanolamine derivatives with maleic acid and then with 2-halocarboxylic acid, to mixtures of chelating agents and methods using such chelating agents.

12 Claims, 1 Drawing Sheet

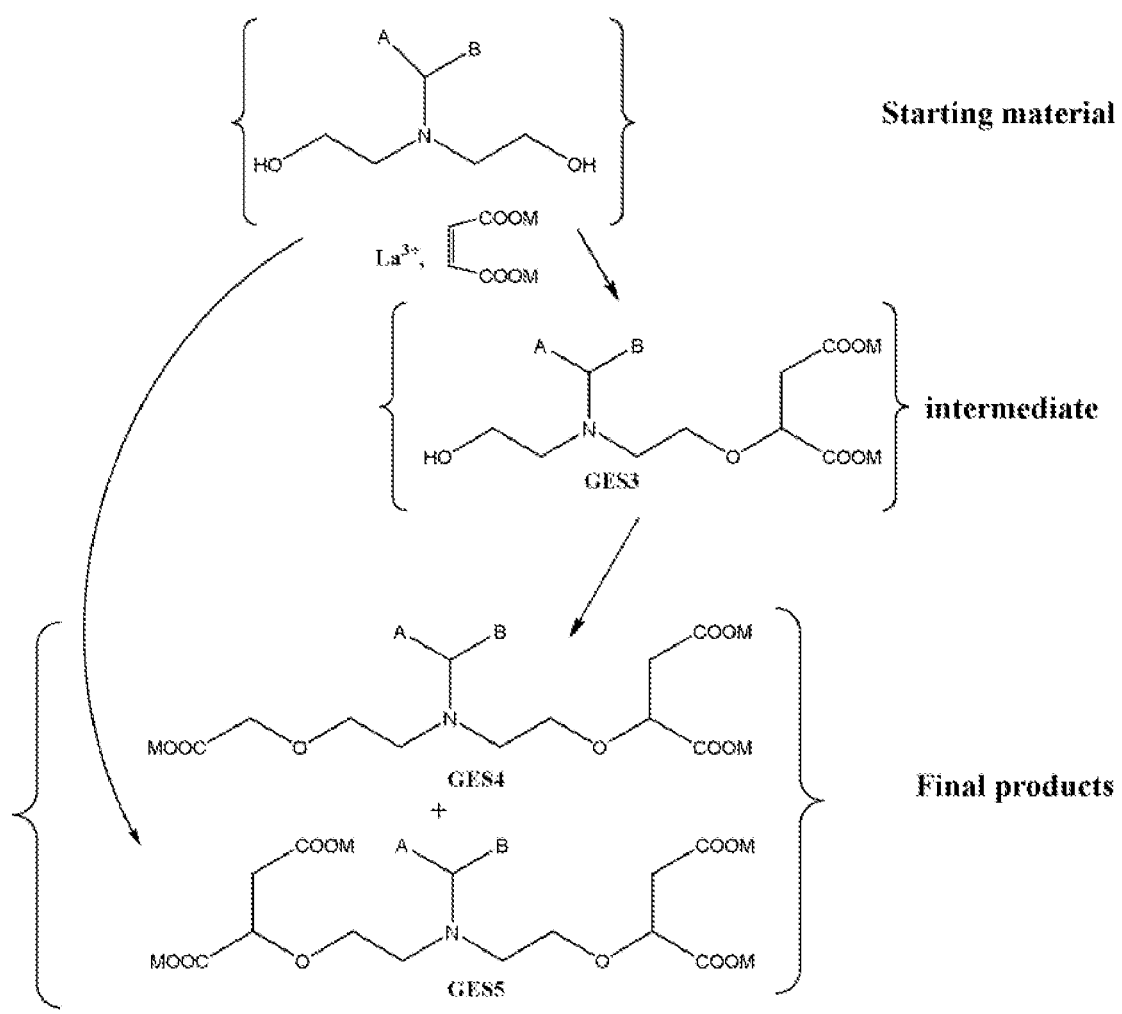

PROCESS FOR THE PREPARATION OF A MIXTURE OF CHELATING AGENTS, MIXTURE OF CHELATING AGENTS AND METHODS OF USING THEM

PRIORITY

This application is a U.S national application of the international application number PCT/FI2018/050505 filed on Jun. 27, 2018 and claiming priority of Finnish national application 20175632 filed on Jun. 30, 2017 the contents of all of which are incorporated herein by reference.

The present invention relates to a process for in situ the preparation of mixtures of chelating agents by catalyzed reactions diethanolamine derivatives with maleic acid and with 2-halocarboxylic acid, to mixtures of chelating agents and methods using such chelating agents.

BACKGROUND

In pulp bleaching liquors, iron and manganese ions are desired to be trapped by a chelating agent, thereby inhibiting these metal ions from catalyzing the decomposition of the bleaching agents, hydrogen peroxide or peroxy acids. Because there is naturally a high concentration of calcium ions in the bleaching liquors, a chelating agent effectively chelating calcium would be consumed by calcium ions. Therefore, chelating agents to selectively complex iron and manganese ions are desired.

WO 97/45396 discloses N-bis- and N-tris-[(1,2-dicarboxy-ethoxy)-ethyl]-amine derivatives including N-bis-[(1,2-dicarboxy-ethoxy)-ethyl]-aspartic acid (also called aspartic acid diethoxy succinate or AES), and the use of these derivatives as chelating agents of metals, especially in connection with pulp bleaching. These derivatives can be prepared by reacting di- or triethanolamine with an alkali metal or alkaline earth metal salt of maleic acid in the presence of a catalyst such as lanthanoid compounds, a nickel compound or alkaline earth metal compounds, e.g. calcium hydroxide or magnesium hydroxide.

A drawback with the above mentioned synthesis of e.g. AES is that the reaction is relatively slow, the reaction time being about 12 to 16 hours, and that the reaction does not go to completion. A typical obtainable conversion from diethanol amine to AES products is about 60 to 70%. Also a significant amount up to about 40 mol-%, of diethanol amine (DEA) used as a starting material, is left unreacted.

In order to simultaneously complex different metal ions in aqueous solutions, it is essential in many applications to have a mixture of chelating agents having different ligand structure. Therefore, there is a need to develop a method for the preparation of mixtures of chelating agents in situ in the same reaction mixture. In addition there is a continuous need for a process where the starting materials are efficiently converted into chelating agents.

SUMMARY OF THE INVENTION

According to the present invention it was surprisingly found that the free hydroxyl groups of bis-(2-hydroxyethyl) glycine or bis-(2-hydroxyethyl)methyl glycine, or salts thereof can easily and effectively be converted into other reactive ingredients by the addition of a maleate into the reaction containing a lanthanoid catalyst to yield an amino acid derivative substituted with succinic acid groups.

It has now been surprisingly found that mixtures of chelating agents having a diethanol amine backbone can be effectively prepared by lanthanoid-catalysed reaction of bis-(2-hydroxyethyl)glycine or bis-(2-hydroxyethyl)methyl glycine, or salts thereof with a maleate followed by a subsequent lanthanide-catalyzed reaction with a 2-halocarboxylic acid.

The first aspect of the invention is a process for the preparation of mixture of chelating agents comprising a compound of Formula (I)

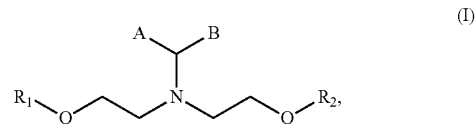

wherein A is H or methyl, B is a carboxylic acid or a salt thereof, and $R_1$ and $R_2$ are H. According to the invention said method comprises reacting the hydroxyl groups of a compound having a general formula (I) wherein A is H or methyl, B is a carboxylic acid or a salt thereof, and $R_1$ and $R_2$ are H with maleic acid or a salt thereof in alkaline conditions in the presence of a lanthanide catalyst to form a mixture comprising compounds a. having a general formula (I) wherein A is H or methyl, B is a carboxylic acid group or a salt thereof, and $R_1$ and $R_2$ are succinic acid groups or a salts thereof, and b. having a general formula (I) wherein A is H or methyl, B is a carboxylic acid group or a salt thereof, and one of $R_1$ and $R_2$ is a succinic acid group or a salt thereof, and the other is an unreacted hydroxyl group followed by adding a 2-halocarboxylic acid or a salt thereof which reacts with intermediates containing unreacted hydroxyl groups to form a mixture comprising the compounds having a general formula (I)

a. having a general formula (I) wherein A is H or methyl, B is a carboxylic acid group or a salt thereof, and $R_1$ and $R_2$ are succinic acid groups or a salts thereof (GES5), and b. having a general formula (I) wherein A is H or methyl, B is a carboxylic acid group or a salt thereof, and one of $R_1$ and $R_2$ is a succinic acid group or a salt thereof, and the other is a carboxymethyl or 1-carboxyethyl group or a salt thereof (GES4).

The second aspect of this invention is a mixture of chelating agents obtained as described here.

The third aspect of this invention is a mixture of chelating agents. According to the invention said mixture comprises at least 50% (w/w) of GES5 and at least 3% (w/w) of GES3.

The fourth aspect of this invention is a method of chelating metals by contacting the mixture here described with an aqueous slurry comprising the metals.

The fifth aspect of this invention is a method of bleaching pulp comprising treating the pulp with the mixture described here or adding the mixture described here to the bleaching stage.

BRIEF DESCRIPTION OF FIGURES

FIGURE shows a simplified reaction scheme for one possible embodiment of the present invention. In the FIGURE, A is H or methyl, B is a carboxylic acid or a salt thereof, and M is H or a metal ion. HA is a 2-halocarboxylic acid.

DETAILED DESCRIPTION

As used herein, the expression "a mixture of chelating agents" means a mixture comprising at least two differently substituted chelating agents synthesized starting from bis-(2-hydroxyethyl)glycine or bis-(2-hydroxyethyl)methyl glycine.

Maleate as used herein means maleic acid or a salt thereof.

As used herein the expression intermediate(s) means compounds having a diethanolamine backbone and a general formula (I) where at least one of $R_1$ or $R_2$ is a succinic acid group, A is H or methyl, B is a carboxylic acid or a salt thereof and the compound contains at least one unreacted/free hydroxyl group.

As used herein the expression succinic acid group means a substituent formed in the Michael-addition of a maleate to a hydroxyl group including both carboxylic acids and salts thereof.

As used herein the term 2-halocarboxylic acid means saturated carboxylic acids substituted with a halogen atom in the 2-position. The carboxylic acid is preferably acetic acid or propionic acid. The halogen is preferably bromine or chlorine.

As used herein the term equilibrium means an ordinary chemical equilibrium of a reaction.

A method for the preparation of mixtures of chelating agents in situ is described here. This method accomplishes the conversion of most of the starting materials to chelating agents. A mixture comprising chelating agents with different capability to complex metal cations is many times advantageous for a complete deactivation of the metal ions in for example pulp bleaching applications. In addition, it is economically and environmentally advantageous to have the starting materials of the chelating agent synthesis reacted as completely as possible to form useful reaction products. In addition the mixture comprising products obtained using the method here described is essentially free of diethanolamine that could form harmful or toxic nitrosamines. The composition of the metal complexing molecules can be easily adjusted by varying the ratios of the reagents used in the synthesis of the mixtures of chelating agents.

The metal complexing ability of mixtures of chelating agents is usually better than the complexing ability of individual chelating agents. This is especially noticed in the pulp bleaching applications, where iron, manganese, calcium and magnesium ions are present in the bleaching liquor.

Compared to traditionally used chelating agents such as ethylenediamine tetraacetic acid (EDTA) and diethylenetriamine pentaacetic acid (DTPA), the chelating agents prepared by the method described here, are more biodegradable. Some of the compounds obtained by this method are readily biodegradable (e.g. ethylenediamine disuccinic acid EDDS and iminodisuccinic acid IDS) and generally the diethanolamine originated polycarboxylic acids are at least inherently biodegradable.

An aspect of the present invention is a process for the preparation of mixture of chelating agents comprising a compound of Formula (I)

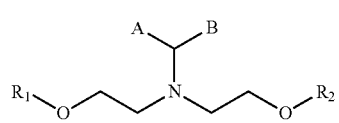

Said process comprises reacting the hydroxyl groups of a compound having a general formula (I) wherein A is H or methyl, B is a carboxylic acid or a salt thereof, and $R_1$ and $R_2$ are H with maleic acid or a salt thereof in alkaline conditions in the presence of a lanthanide catalyst to form a mixture comprising compounds
   a. having a general formula (I) wherein A is H or methyl, B is a carboxylic acid group or a salt thereof, and $R_1$ and $R_2$ are succinic acid groups or a salts thereof (GES5 or MGES5), and
   b. having a general formula (I) wherein A is H or methyl, B is a carboxylic acid group or a salt thereof, and one of $R_1$ and $R_2$ is a succinic acid group or a salt thereof, and the other is an unreacted hydroxyl group (GES3 or MGES3)

followed by adding a 2-halocarboxylic acid or a salt thereof which reacts with intermediates containing unreacted hydroxyl groups to form a mixture comprising the compounds having a general formula (I)
   a. having a general formula (I) wherein A is H or methyl, B is a carboxylic acid group or a salt thereof, and $R_1$ and $R_2$ are succinic acid groups or a salts thereof (GES5 or MGES5), and
   b. having a general formula (I) wherein A is H or methyl, B is a carboxylic acid group or a salt thereof, and one of $R_1$ and $R_2$ is a succinic acid group or a salt thereof, and the other is a carboxymethyl or 1-carboxyethyl group or a salt thereof (GES4 or MGES4).

In this connection the expression "carboxymethyl or 1-carboxyethyl group or a salt thereof" means monocarboxylic acid group (or a salt thereof) derived from the reaction of a hydroxyl group or secondary amine group with a 2-haloalkylcarboxylic acid or a salt thereof.

In one embodiment, bis-(2-hydroxyethyl)glycine or bis-(2-hydroxyethyl)methyl glycine is formed by reacting diethanolamine with a 2-halocarboxylic acid or a salt thereof.

In one embodiment the reaction is continued until the reaction mixture further contains compounds having a general formula (I) wherein A is H or methyl, B is a carboxylic acid group or a salt thereof, $R_1$ is a succinic acid group or a salt thereof and $R_2$ is a hydroxyl group (GES 3 or MGES3).

In one embodiment the 2-halocarboxylic acid used in the reaction is bromo- or chloroacetic acid, preferably 2-chloroacetic acid. In another embodiment, the 2-halocarboxylic acid is 2-chloro- or 2-bromopropionic acid, preferably 2-chloropropionic acid.

Chlorine containing starting materials are preferred due to the difficulties in recycling hydrobromic acid formed in the reaction. Furthermore, colored bromine containing side-products which are undesirable in pulping applications are formed.

The non-catalyzed reaction of 2-halocarboxylic acids with an amino group is known in the literature. This reaction is usually carried out in an alkaline aqueous solution. Side reactions, e.g. hydrolysis of 2-halocarboxylic acid to the respective 2-hydroxy carboxylic acids are also well-known. A conversion of the unreacted hydroxyl groups of the chelating agent intermediates by non-catalyzed alkylation after the incomplete reaction result in a sluggish and incomplete reaction. The alkylation of hydroxyl groups with 2-halocarboxylic acids usually requires strong bases and again, the reactions proceed incompletely.

Lanthanoid-catalyzed Michael additions of hydroxyl groups to maleate are known in the past literature. It has now been surprisingly found that it is possible to convert the free hydroxyl groups in a complex mixture of polycarboxylic acids to the respective succinic acid derivatives by a lanthanoid catalyzed addition of the hydroxyl group with 2-halocarboxylic acid. The previous efforts of the inventors to convert diethanolamine derivatives to the corresponding O-alkylated carboxymethyl derivatives have failed when 2-haloalkyl carboxylic acids were used in the absence of a lanthanoid catalyst.

The lanthanoid (previously named lanthanide) series comprises the fifteen elements with atomic numbers from 57 to 71. Preferred lanthanoid catalysts are lanthanum (La), praseodymium (Pr), neodymium (Nd), europium (Eu), dysprosium Dy), Erbium (Er) and ytterbium (Yb). The elements of the lanthanoid series may be used in the form of oxides or salts including carbonates, nitrates, chlorides, maleates and octanoates.

Residual lanthanide ions/salts are removed from the reaction mixture by methods known in the literature. Such methods can be precipitation as carbonates or oxalates followed by the removal of the precipitate by filtration or centrifugation.

In one embodiment the catalyst is a lanthanoid catalyst including lanthanum(III)oxide and lanthanum(III)salts, such as lanthanum carbonate, lanthanum maleate, lanthanum nitrate, lanthanum chloride or lanthanum octanoate. Michael additions of amino groups to maleate proceed to some extent without a catalyst. Lanthanoids also catalyze hydroamination of maleates. The reaction time of the addition of maleate for example to ethylenediamine has been shortened from 16 hours to one hour by using lanthanoids as catalysts.

The reactions described here are catalyzed by a lanthanoid catalyst. Thus there is no need to remove or change the catalyst during the process. However, in on embodiment lanthanoid catalyst is gradually added to the mixture during the process (reactions) in order to further increase the yield.

In one embodiment the initial molar ratio of the lanthanoid catalyst to bis-(2-hydroxyethyl)glycine or bis-(2-hydroxyethyl)methyl glycine is between 0.5:1 to 1.5:1. The relatively large amount of catalyst is needed as some of the lanthanide is chelated by the formed products.

In one embodiment the ratio of added maleic acid or a salt thereof to bis-(2-hydroxyethyl)glycine or bis-(2-hydroxyethyl)methyl glycine is 1.5:1 to 2.5:1, preferably 2:1. Such ratios enable complete conversion of unreacted hydroxyl groups and secondary amines into carboxylic acid groups.

In one embodiment of the invention bis-(2-hydroxyethyl) glycine or bis-(2-hydroxyethyl)methyl glycine is synthesized from diethanol amine and a 2-halocarboxylic acid, preferably 2-chloroacetic acid or 2-chloropropionic acid.

One possible simplified reaction scheme is illustrated in FIG. 1. In FIG. 1, A is H or methyl, B is a carboxylic acid or a salt thereof, and M is H or a metal ion. HA is a 2-halocarboxylic acid.

In one possible embodiment, dietanolamine is first reacted with 2-chlorocarboxylic acid in a lanthanide-catalyzed reaction to form bicine, followed by a lanthanide-catalyzed addition of maleate to bicine to form a mixture of glycine diethoxysuccinate (GES5) and 2-(2-((carboxymethyl)(2-hydroxyethyl)-amino)ethoxy)succinic acid (GES3), followed by a lanthanum catalyzed addition of 0-alkylation of (GES3) to 2-(2-((2-(carboxymethoxy)ethyl)(carboxymethyl)amino) ethoxy)succinic acid (GES 4).

The initial molar ratio of the lanthanoid catalyst to maleate is preferably between 1:1.5 to 1:5, more preferably between 1:3 and 1:4. Expression "initial molar ratio" herein means the ratio when the reaction between unreacted intermediates containing hydroxyl groups and is started, i.e. when said maleate is added to the reaction mixture.

After completing the reaction, the catalyst is separated using methods known within the field. The catalyst can by separated from the reaction mixture by precipitation as a carbonate by the addition a carbonate salt or carbon dioxide, or as precipitation as an oxalate by the addition of oxalic acid. The formed precipitation can be separated by filtration or centrifugation followed by collecting the supernatant.

The individual components (intermediates or final reaction products) of the mixture are preferably obtained as alkali metal salts or alkaline earth metal salts, but the components may also be obtained in acid form or may be converted from salts into acids.

The present disclosure relates also to a mixture of chelating agents obtained by the process described here.

Further the present disclosure relates to a mixture of chelating agents comprising at least GES5 and GES4. In one embodiment the mixture comprises at least 50 (w/w) of GES5 and at least 2% (w/w) of GES4. In one embodiment the mixture further comprises GES3. In one embodiment amount of GES3 is at least 2% (w/w).

Table below shows one illustrative composition of the mixture described here.

TABLE 1

| | % w/w from the dry matter |
|---|---|
| GES3 | 3 to 12 |
| GES4 | 2 to 6 |
| GES5 | 50 to 95 |

When oxygen or peroxide compounds are used in bleaching of pulp it is important to remove the transition metals from the fiber before bleaching, since transition metal ions catalyze the decomposition of peroxy compounds, thus forming radical compounds. As a consequence of these reactions the strength and brightness properties of the fiber are deteriorated. The decomposition of hydrogen peroxide is catalyzed by transition metals; iron, manganese, and copper are of particular importance in pulp bleaching. The use of chelating agents to remove some of these metal ions from the pulp prior to adding peroxide allows peroxide to be used more efficiently. A chelating agent can be used directly in the bleaching to deactivate metal ions or as a pretreatment before the bleaching. This is especially the case when a multistage peroxide bleaching is employed.

The present disclosure relates also to a method of chelating metals by contacting a mixture of chelating agents described here with an aqueous slurry comprising the metals.

The present disclosure relates also to a method of bleaching pulp comprising treating the pulp by a mixture of chelating agents here described or adding the mixture here described to the bleaching state.

It should be understood, that the embodiments given in the description above are for illustrative purposes only, and that various changes and modifications are possible within the scope of the disclosure. It is also to be understood that the terminology employed herein is for the purpose of description and should not be regarded as limiting. The features described here as separate embodiments may also be provided in combination in a single embodiment. Also various features described here in the context of a single embodiment, may also be provided separately or in any suitable sub-combination.

The invention is described below with the help of examples. The examples are given only for illustrative purpose and they do not limit the scope of the invention.

EXAMPLES

Example 1

Maleic acid solution was prepared by dissolving maleic anhydride (16.77 g, 0.17 mol) was in 80 g of water and by allowing the temperature of the reaction mixture to raise up to 50° C., Lanthanum oxide 9.12 g, 0.028 mol) was dissolved to the maleic maleic acid solution at 50° C. Bicine (13.87 g, 0.085 mol) was added to the reaction mixture and sodium hydroxide (0.285 mol, 22.80 g) was added to the reaction mixture.

The reaction mixture was stirred for 3 hours at 90-95° C., cooled to 50° C. and divided to two equal portions A and B.

Lanthanum catalyst was precipitated from the reaction product portion A. The reaction product was analysed by gas chromatograph as silyl derivatives. The final concentrations of the effective ingredients were (% w/w from the dry matter):

TABLE 2

| | % w/w from the dry matter |
|---|---|
| GES3 | 12.22 |
| GES4 | 0 |
| GES5 | 79.69 |

Example 2

The reaction product, portion A, after precipitation of the catalyst, was treated with 2-chloroacetic acid (1.03 g, 0.011 mol) and the reaction mixture was heated at 80° C. for 1 hours. The reaction product was analysed by gas chromatograph as silyl derivatives. The final concentrations of the effective ingredients were (% w/w from the dry matter):

TABLE 3

| | % w/w from the dry matter |
|---|---|
| GES3 | 12.31 |
| GES4 | 0 |
| GES5 | 79.59 |

Example 3

The reaction product, portion B, still containing the lanthanum catalyst, was treated with 2-chloroacetic acid (1.03 g, 0.011 mol) and the reaction mixture was heated at 80° C. for 1 hours. The reaction product was analysed by gas chromatograph as silyl derivatives. The final concentrations of the effective ingredients were (% w/w from the dry matter):

TABLE 4

| | % w/w from the dry matter |
|---|---|
| GES3 | 7.32% |
| GES4 | 4.53% |
| GES5 | 78.64% |

Example 1 clearly show that the lanthanum catalyzed Michael addition may not go to completion to produce only the effective chelating agent GES5. The reaction product still contains GES3, a reaction product of a partially reacted bicine.

Example 2 shows that the alkylation of GES3 to GES 4 does not occur by addition of 2-halocarboxylic acid in the absence of a lanthanum catalyst.

Example 3 shows that when the 2-halocarboxylic acid is added in the presence of lanthanum catalyst, the alkylation of the free hydroxyl group of GES3 occurs and GES4 is produced. Therefore, the percentage of the effective chelating agents GES 4 and GES5 is 83.16% increased by almost 5 percents. It must be noted that this reaction is not optimized. By optimizing the reaction conditions, the alkylation O-alkylation reaction should proceed into completion.

The invention claimed is:
1. A process for the preparation of a mixture of at least two chelating agents
the process comprising a first step of reacting the hydroxyl groups of a compound having a formula (Ia)

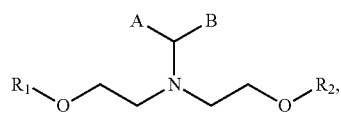

(Ia)

wherein A is H or methyl, B is a carboxylic acid group or a salt thereof, and $R_1$ and $R_2$ are H, with maleic acid or a salt thereof in alkaline conditions in the presence of a lanthanide catalyst to form a mixture comprising
a. compounds having formula (Ib)

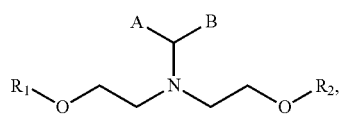

(Ib)

wherein A is H or methyl, B is a carboxylic acid group or a salt thereof, and $R_1$ and $R_2$ are succinic acid groups or salts thereof, and
b. compounds having formula (Ic)

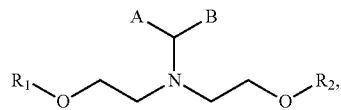

(Ic)

wherein A is H or methyl, B is a carboxylic acid group or a salt thereof, and one of $R_1$ and $R_2$ is a succinic acid group or a salt thereof, and the other is H,
followed by a second step of adding a 2-halocarboxylic acid or a salt thereof which reacts with intermediates having formula (Ic) to form a mixture comprising
a. compounds having formula (Id)

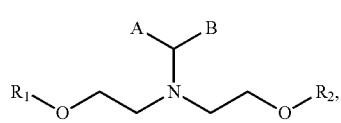

(Id)

wherein A is H or methyl, B is a carboxylic acid group or a salt thereof, and $R_1$ and $R_2$ are succinic acid groups or a salts thereof (GES5), and b. compounds having formula (Ie)

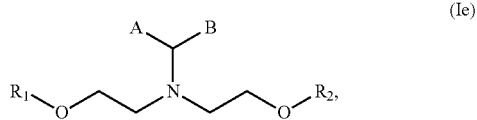

(Ie)

wherein A is H or methyl, B is a carboxylic acid group or a salt thereof, and one of $R_1$ and $R_2$ is a succinic acid group or a salt thereof, and the other is a carboxymethyl or 1-carboxyethyl group or a salt thereof (GES4).

2. The process of claim 1, wherein said mixture of at least two chelating agents further contains compounds having a formula (If)

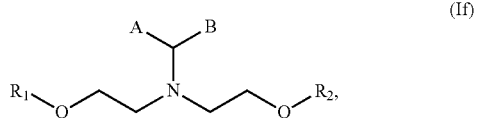

(If)

wherein A is H or methyl, B is a carboxylic acid group or a salt thereof, $R_1$ is a succinic acid group or a salt thereof and $R_2$ is H (GES 3).

3. The process of claim 1, wherein the 2-halocarboxylic acid is bromo- or chloroacetic acid.

4. The process of claim 1, wherein the 2-halocarboxylic acid is a 2-chloro- or 2-bromopropionic acid.

5. The process of claim 1, wherein the lanthanide catalyst comprises lanthanum(lll)oxide and lanthanum(lll)salts.

6. The process of claim 1, wherein in Formula (Ia) B is —COOH or a salt thereof and an initial molar ratio of the lanthanide catalyst to the compound having the Formula (Ia) is between 0.5:1 to 1.5:1.

7. The process of claim 1, wherein in Formula (Ia) B is —COOH or a salt thereof and a molar ratio of added maleic acid or a salt thereof to the compound having Formula (Ia) is 1.5:1 to 2.5:1.

8. The process of claim 2, wherein the mixture of at least two chelating agents comprises at least 50% (w/w) of GES5 and at least 3% (w/w) of GES3.

9. The process of claim 3, wherein the 2-halocarboxylic acid is 2-chloroacetic acid.

10. The process of claim 4, wherein the 2-halocarboxylic acid is 2-chloropropionic acid.

11. The process of claim 7, wherein the molar ratio of added maleic acid or a salt thereof to the compound having Formula (Ia) is 2:1.

12. The process of claim 5, wherein the lanthanide catalyst is a lanthanum (III) salt selected from the group consisting of lanthanum carbonate, lanthanum maleate, lanthanum nitrate, lanthanum chloride and lanthanum octanoate.

* * * * *